US010238399B2

(12) United States Patent
Fox et al.

(10) Patent No.: US 10,238,399 B2
(45) Date of Patent: *Mar. 26, 2019

(54) DISTAL FEMORAL CUTTING GUIDE

(71) Applicant: Biomet Manufacturing, LLC, Warsaw, IN (US)

(72) Inventors: Duke A. Fox, Warsaw, IN (US); Robert Metzger, Wakarusa, IN (US); Scott Twomey, Fort Wayne, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/787,159

(22) Filed: Oct. 18, 2017

(65) Prior Publication Data

US 2018/0036014 A1 Feb. 8, 2018

Related U.S. Application Data

(60) Continuation of application No. 14/802,354, filed on Jul. 17, 2015, now Pat. No. 9,826,982, which is a
(Continued)

(51) Int. Cl.
*A61B 17/15* (2006.01)
*A61B 17/17* (2006.01)

(52) U.S. Cl.
CPC ........ *A61B 17/155* (2013.01); *A61B 17/1764* (2013.01)

(58) Field of Classification Search
CPC .......................... A61B 17/155; A61B 17/1764
See application file for complete search history.

(56) References Cited

U.S. PATENT DOCUMENTS 4,487,203 A * 12/1984 Androphy ............ A61B 17/154
33/512
4,567,885 A 2/1986 Androphy
(Continued)

FOREIGN PATENT DOCUMENTS

FR 2679766 A1 2/1993

OTHER PUBLICATIONS

"U.S. Appl. No. 11/717,793, Examiner Interview Summary dated Aug. 20, 2010", 3 pgs.
(Continued)

*Primary Examiner* — Christian Sevilla
(74) *Attorney, Agent, or Firm* — Schwegman Lundberg & Woessner, P.A.

(57) ABSTRACT

A method of positioning a femoral cutting guide on a distal end of a femur establishes at least a first reference plane to perform a distal femoral planar cut. The method includes inserting a mounting member into an intramedullary canal of the femur and coupling a bridge member to the mounting member. The method also includes placing a cutting guide member over a medal anterior portion of the distal femur. The cutting guide member has a first channel that establishes the first reference plane. The bridge member has a bridge channel. A wall of the bridge channel is inserted into the first channel of the cutting guide member. A mounting mechanism generates resistance between the bridge member and the cutting guide member. The resistance is overcome by positioning the cutting guide member relative to the femur.

20 Claims, 7 Drawing Sheets

Related U.S. Application Data continuation of application No. 13/716,914, filed on Dec. 17, 2012, now Pat. No. 9,113,923, which is a division of application No. 13/116,530, filed on May 26, 2011, now Pat. No. 8,333,772, which is a division of application No. 11/717,793, filed on Mar. 13, 2007, now Pat. No. 7,959,637.

(56) References Cited

U.S. PATENT DOCUMENTS

| | | | |
|---|---|---|---|
| 4,676,570 A | | 6/1987 | Pincherri |
| 4,703,751 A | * | 11/1987 | Pohl ............... A61B 17/155 |
| | | | 606/53 |
| 4,759,350 A | | 7/1988 | Dunn et al. |
| 4,773,407 A | | 9/1988 | Petersen |
| 4,907,578 A | | 3/1990 | Petersen |
| 4,940,452 A | | 7/1990 | Rohe et al. |
| 4,952,213 A | * | 8/1990 | Bowman ............ A61B 17/157 |
| | | | 606/62 |
| 5,002,545 A | | 3/1991 | Whiteside et al. |
| 5,078,719 A | * | 1/1992 | Schreiber ............ A61B 17/152 |
| | | | 606/87 |
| 5,092,869 A | | 3/1992 | Waldron |
| 5,234,433 A | | 8/1993 | Bert et al. |
| 5,342,367 A | | 8/1994 | Ferrante et al. |
| 5,342,368 A | | 8/1994 | Petersen |
| 5,364,402 A | | 11/1994 | Mumme et al. |
| 5,423,822 A | | 6/1995 | Hershberger et al. |
| 5,474,559 A | | 12/1995 | Bertin et al. |
| 5,484,446 A | | 1/1996 | Burke et al. |
| 5,486,178 A | * | 1/1996 | Hodge ............... A61B 17/155 |
| | | | 606/102 |
| 5,540,696 A | | 7/1996 | Booth, Jr. et al. |
| 5,569,260 A | | 10/1996 | Petersen |
| 5,611,802 A | | 3/1997 | Samuelson et al. |
| 5,628,750 A | | 5/1997 | Whitlock et al. |
| 5,658,293 A | | 8/1997 | Vanlaningham |
| 5,662,656 A | * | 9/1997 | White ............... A61B 17/155 |
| | | | 606/86 R |
| 5,667,511 A | | 9/1997 | Vendrely et al. |
| 5,676,668 A | | 10/1997 | McCue et al. |
| 5,681,316 A | | 10/1997 | DeOrio et al. |
| 5,720,750 A | | 2/1998 | Koller et al. |
| 5,722,978 A | | 3/1998 | Jenkins, Jr. |
| 5,776,137 A | | 7/1998 | Katz |
| 5,782,918 A | | 7/1998 | Klardie et al. |
| 5,817,097 A | | 10/1998 | Howard et al. |
| 5,830,216 A | | 11/1998 | Insall et al. |
| 5,910,143 A | | 6/1999 | Cripe et al. |
| 6,013,081 A | | 1/2000 | Burkinshaw et al. |
| 6,024,746 A | | 2/2000 | Katz |
| 6,059,788 A | | 5/2000 | Katz |
| 6,090,114 A | | 7/2000 | Matsuno et al. |
| 6,193,723 B1 | | 2/2001 | Cripe et al. |
| 6,241,731 B1 | | 6/2001 | Fiz et al. |
| 6,514,259 B2 | | 2/2003 | Picard et al. |
| 6,575,980 B1 | | 6/2003 | Robie et al. |
| 6,632,225 B2 | | 10/2003 | Sanford et al. |
| 6,740,092 B2 | | 5/2004 | Lombardo et al. |
| 7,104,997 B2 | | 9/2006 | Lionberger et al. |
| 7,241,298 B2 | | 7/2007 | Nemec et al. |
| 7,520,880 B2 | | 4/2009 | Claypool et al. |
| 7,618,420 B2 | | 11/2009 | Collazo |
| 7,618,421 B2 | | 11/2009 | Axelson, Jr. et al. |
| 7,959,637 B2 | | 6/2011 | Fox et al. |
| 8,333,772 B2 | | 12/2012 | Fox et al. |
| 9,113,923 B2 | | 8/2015 | Fox et al. |
| 9,826,982 B2 | | 11/2017 | Fox et al. |
| 2004/0102785 A1 | | 5/2004 | Hodorek et al. |
| 2004/0153083 A1 | | 8/2004 | Nemec et al. |
| 2004/0176797 A1 | | 9/2004 | Opolski |
| 2004/0236341 A1 | | 11/2004 | Petersen |
| 2005/0154394 A1 | | 7/2005 | Michalowicz |
| 2006/0200158 A1 | | 9/2006 | Farling et al. |
| 2006/0200163 A1 | | 9/2006 | Roger et al. |
| 2006/0241634 A1 | | 10/2006 | Tuttle et al. |
| 2007/0288030 A1 | | 12/2007 | Metzger et al. |
| 2008/0228189 A1 | | 9/2008 | Fox et al. |
| 2009/0043310 A1 | | 2/2009 | Rasmussen |
| 2013/0178859 A1 | | 7/2013 | Fox et al. |
| 2015/0359545 A1 | | 12/2015 | Fox et al. |

OTHER PUBLICATIONS

"U.S. Appl. No. 11/717,793, Final Office Action dated Dec. 17, 2010", 18 pgs.
"U.S. Appl. No. 11/717,793, Non Final Office Action dated Feb. 4, 2010", 12 pgs.
"U.S. Appl. No. 11/717,793, Non Final Office Action dated Jul. 21, 2010", 14 pgs.
"U.S. Appl. No. 11/717,793, Notice of Allowance dated Feb. 7, 2011", 4 pgs.
"U.S. Appl. No. 11/717,793, Preliminary Amendment filed Nov. 13, 2009", 9 pgs.
"U.S. Appl. No. 11/717,793, Response filed Feb. 3, 2011 to Final Office Action dated Dec. 17, 2010", 6 pgs.
"U.S. Appl. No. 11/717,793, Response filed May 3, 2010 to Non Final Office Action dated Feb. 4, 2010", 15 pgs.
"U.S. Appl. No. 11/717,793, Response filed Oct. 12, 2010 to Non Final Office Action dated Jul. 21, 2010", 16 Pgs.
"U.S. Appl. No. 11/717,793, Response filed Nov. 2, 2009 to Restriction Requirement dated Oct. 1, 2009", 1 pg.
"U.S. Appl. No. 11/717,793, Restriction Requirement dated Oct. 1, 2009", 7 pgs.
"U.S. Appl. No. 13/116,530, Notice of Allowance dated Aug. 15, 2012", 9 pgs.
"U.S. Appl. No. 13/716,914, Notice of Allowance dated Apr. 20, 2015", 7 pgs.
"U.S. Appl. No. 14/802,354, Non Final Office Action dated Mar. 10, 2017", 5 pgs.
"U.S. Appl. No. 14/802,354, Notice of Allowance dated Jul. 26, 2017", 7 pgs.
"U.S. Appl. No. 14/802,354, Response filed May 19, 2017 to Non-Final Office Action dated Mar. 10, 2017", 10 pgs.

* cited by examiner

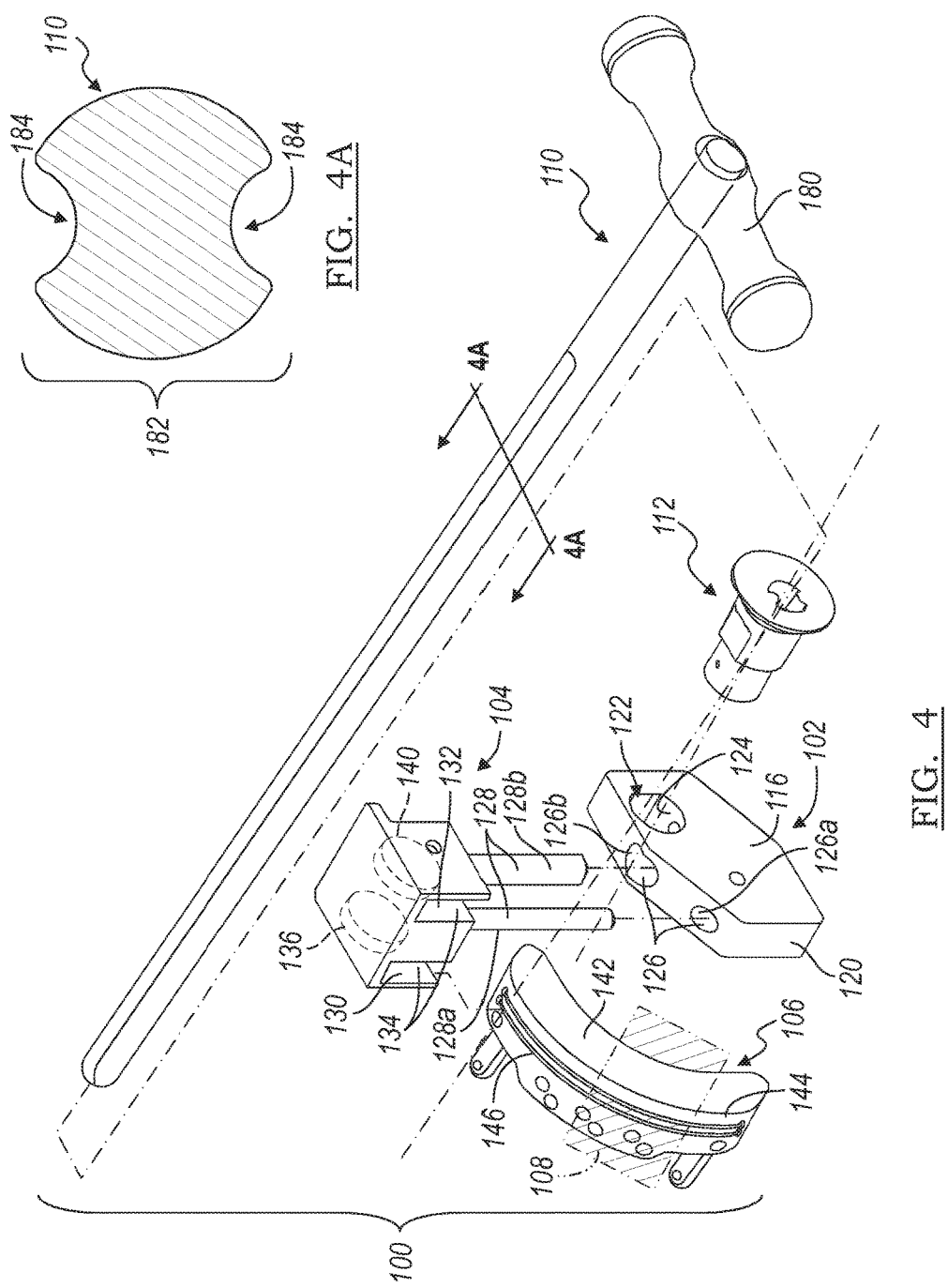

DISTAL FEMORAL CUTTING GUIDE

CROSS-REFERENCE TO RELATED APPLICATIONS

This application is a continuation of U.S. patent application Ser. No. 14/802,354, filed on Jul. 17, 2015, now issued as U.S. Pat. No. 9,826,982, which is a continuation of U.S. patent application Ser. No. 13/716,914, filed on Dec. 17, 2012, now issued as U.S. Pat. No. 9,113,923, which is a divisional of U.S. patent application Ser. No. 13/116,530 filed on May 26, 2011, now issued as U.S. Pat. No. 8,333,772, which is a divisional of U.S. patent application Ser. No. 11/717,793 filed on. Mar. 13, 2007, now U.S. Pat. No. 7,959,637 issued on Jun. 14, 2011. The entire disclosure of the above application is incorporated herein by reference.

FIELD

The present teachings relate to a cutting guide for resecting a portion of a bone and more particularly relate to a distal femoral cutting guide that can be selectively adjusted over a medial anterior portion of a distal end of a femur.

BACKGROUND

A human joint 10 is the junction of four bones: a femur 12, a tibia 14, a fibula 16 and a patella 18, as shown in FIGS. 1-3. Myriad medical problems can require partial or complete replacement of one or more portions of the aforesaid bones that form the knee joint 10. When using one or more prosthetic devices to replace one or more portions of the bones of the knee joint 10, preparation portions of the various bones can be necessary to supply a proper fit for the prosthetic. Preparation can include resection or fashioning of the bones to complement an interior portion of a prosthetic.

When implanting a prosthetic on a distal end 20 of the femur 12, portions of the distal end 20 can be resected to provide a proper fit for the prosthetic. For example, a lateral condyle 22 and a medial condyle 24 can be partially or completely resected in preparation for implantation of the prosthetic. A distal femoral planar cut is generally performed relative to a mechanical angle of the knee joint 10. To vary the angle of the distal femoral planar cut, multiple components typically have to be disassembled and reassembled to provide the proper angle. One or more of the components used to provide the distal femoral planar cut are typically positioned above an anterior surface of the femur. In such a position, access to an anterior portion of the femur and positioning components in the same area can be relatively difficult. While the above methods and components remain useful for their intended purpose, there remains room in the art for improvement.

SUMMARY

The present teachings generally include a system that locates a femoral cutting guide on a distal end of a femur. The femoral cutting guide establishes at least a first reference plane to perform a distal femoral planar cut. The system generally includes a mounting rod operable to insert into the distal end of the femur. An index member is operable to abut the distal end of the femur. A bridge member extends from the index member. A cutting guide member extends from the bridge member. The cutting guide member includes a first channel that establishes the first reference plane. A mounting mechanism releasable couples the cutting guide member to the bridge member. The mounting mechanism is operable to generate a sliding resistance between the bridge member and the cutting guide member that is generally overcome to position the cutting guide member relative to the femur.

The present teachings provide a method of positioning a femoral cutting guide on a distal end of a femur to establish at least a first reference plane to perform a distal femoral planar cut. The method includes inserting a mounting member into an intramedullary canal of the femur and coupling a bridge member to the mounting member. The method also includes placing a cutting guide member over a medial anterior portion of the distal femur. The cutting guide member has a first channel that establishes the first reference plane. The bridge member has a bridge channel. A wall of the bridge channel is inserted into the first channel of the cutting guide member. A mounting mechanism generates resistance between the bridge member and the cutting guide member. The resistance is overcome by positioning the cutting guide member relative to the femur.

In some embodiments the method includes passing a mounting rod into a keyed bushing coupled to an offset opening through first and second opposing surfaces of an index member and inserting the mounting rod into an intramedullary canal of the femur. The method also includes inserting first and second elongated posts of a bridge member into corresponding first and second apertures in a peripheral wall of the index member and the first and second elongated posts having different cross-sections and placing a cutting guide member over a medial anterior corner of the distal femur. The bridge member has a bridge channel. A wall of the bridge channel is inserted into a channel of the cutting guide member. The first surface of the index member is engaged to the distal end of the femur when the femur is a right femur. The second surface of the index member is engaged to the distal end of the femur when the femur is a left femur.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and do not limit the scope of the present teachings.

FIG. 4 is an exploded assembly view of a distal femoral cutting guide assembly constructed in accordance with the present teachings having an index member, a bridge member and a guide member that can couple to an intramedullary rod with a bushing coupled to the index member.

FIG. 4A is a cross-sectional view taken along line 4A-4A of FIG. 4.

DETAILED DESCRIPTION

Figure 1:
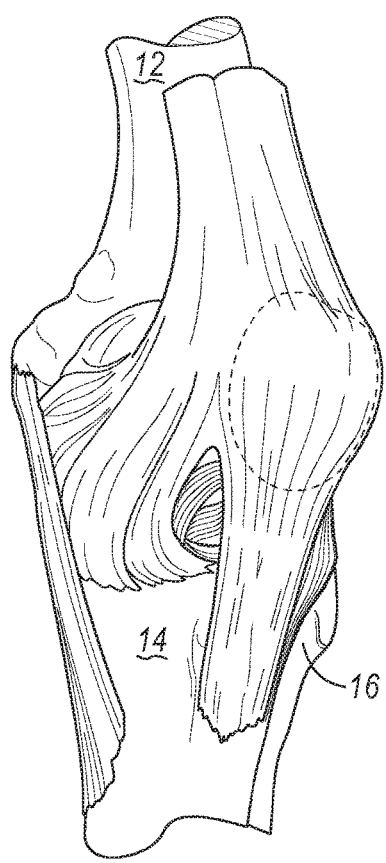
FIG. 1 is a prior art partial front view of a knee joint showing bones, muscle tissue and connective tissue of the knee joint.
Figure 2:
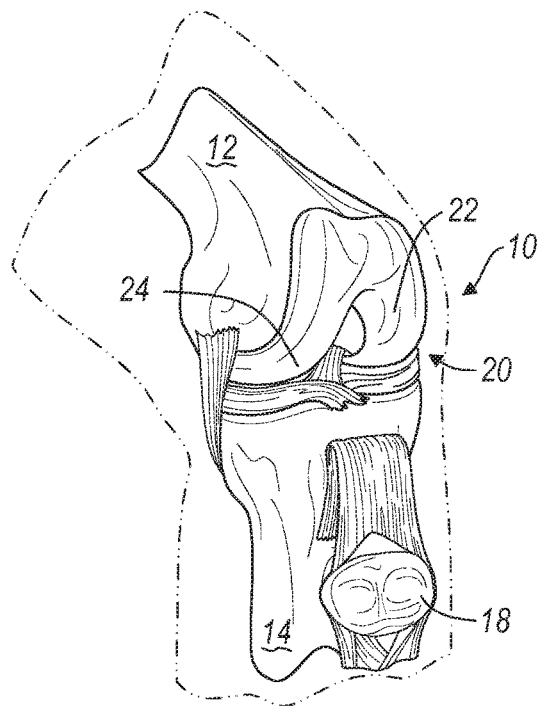
FIG. 2 is a prior art similar to FIG. 1 and shows a patella, the muscles and the associated connective tissue pulled away from respective portions of the knee joint.

The following description is merely exemplary in nature and is not intended to limit the present teachings, their application, or uses. It should be understood that throughout the drawings, corresponding reference numerals can indicate like or corresponding parts and features.

The present teachings generally include a cutting guide assembly 100 for resecting a portion of a bone, as shown in FIG. 4. While the various illustrated aspects of the present teachings pertain to the knee joint 10 (FIG. 3) of the human body, it will be appreciated in light of the disclosure that the teachings may also be applicable to various bones of the human body including, but not limited to, the tibia, the fibula, the humerus, the ulna or the radius. It will also be appreciated that the teachings may be applicable to various bones of other animals, mammalian or otherwise, requiring replacement with prosthetics due to various medical concerns.

Figure 5A:
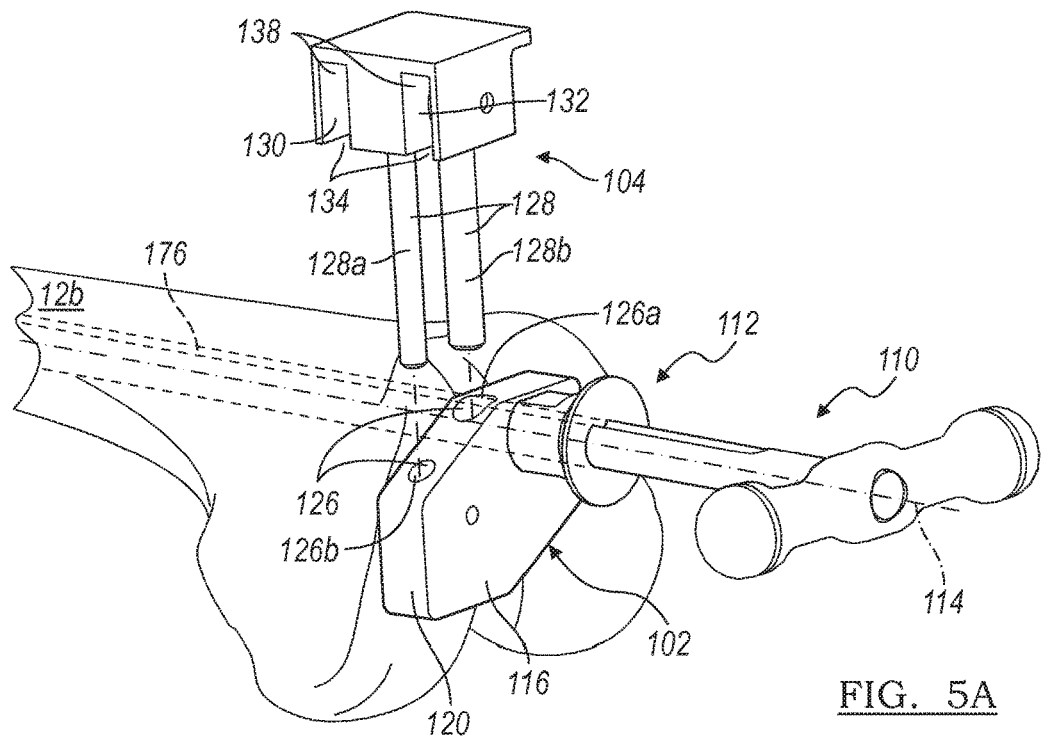
FIG. 5A is a partial perspective view of the bushing installed in the index member and disposed over the intramedullary rod of FIG. 4 that is installed on the left femur in accordance with the present teachings.
Figure 5B:
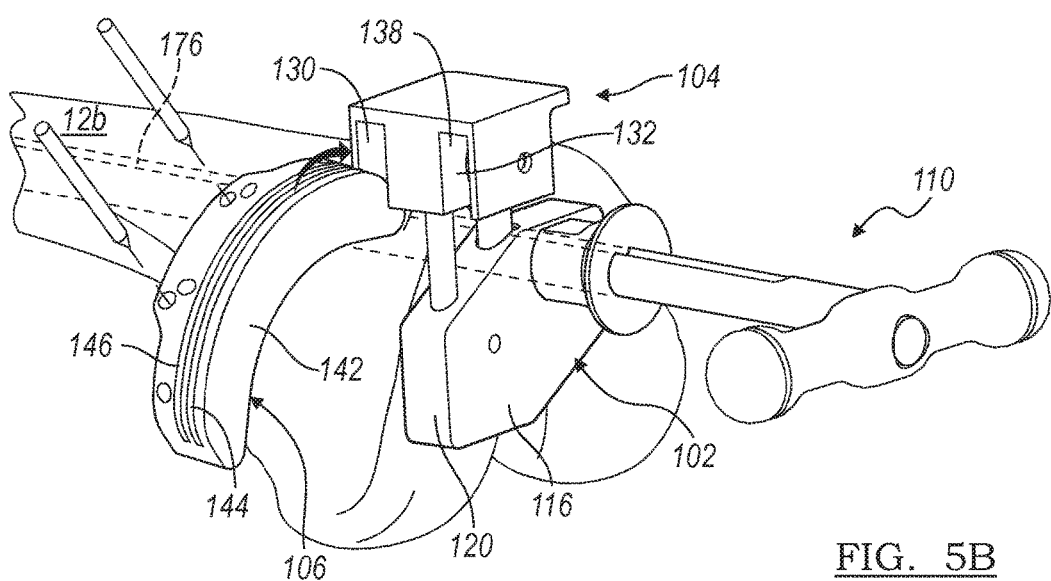
FIG. 5B is similar to FIG. 5A and shows the bridge member connected to the index member and receiving the guide member to hold the guide member so that the cutting guide member can be further secured to the bone with suitable fixation pins in a first set of apertures in accordance with the present teachings.

With reference to FIG. 4, the cutting guide assembly 100 can include an index member 102, a bridge member 104 and a cutting guide member 106. The cutting guide assembly 100 can be used in a procedure to resect (i.e., surgically remove part of an organ or a structure) one or more portions of a distal end of a right femur 12a (FIG. 6) and/or a left femur 12b (FIGS. 5A-5E), which can be collectively referred to as the distal end 20 of the femur 12. As shown in FIG. 5A, the index member 102 can abut the distal end 20 of the femur 12. As shown in FIG. 5B, the bridge member 104 can couple the cutting guide member 106 to the index member 102 and can establish a reference plane 108 (an imaginary plane, as shown in FIG. 4) that can project through the distal end 20 of the femur 12. While the bridge member 104 is shown as a separate component, in one example, the bridge member 104 and the cutting guide member 106 can be a single monolithic member or a collection of multiple components.

Figure 6:
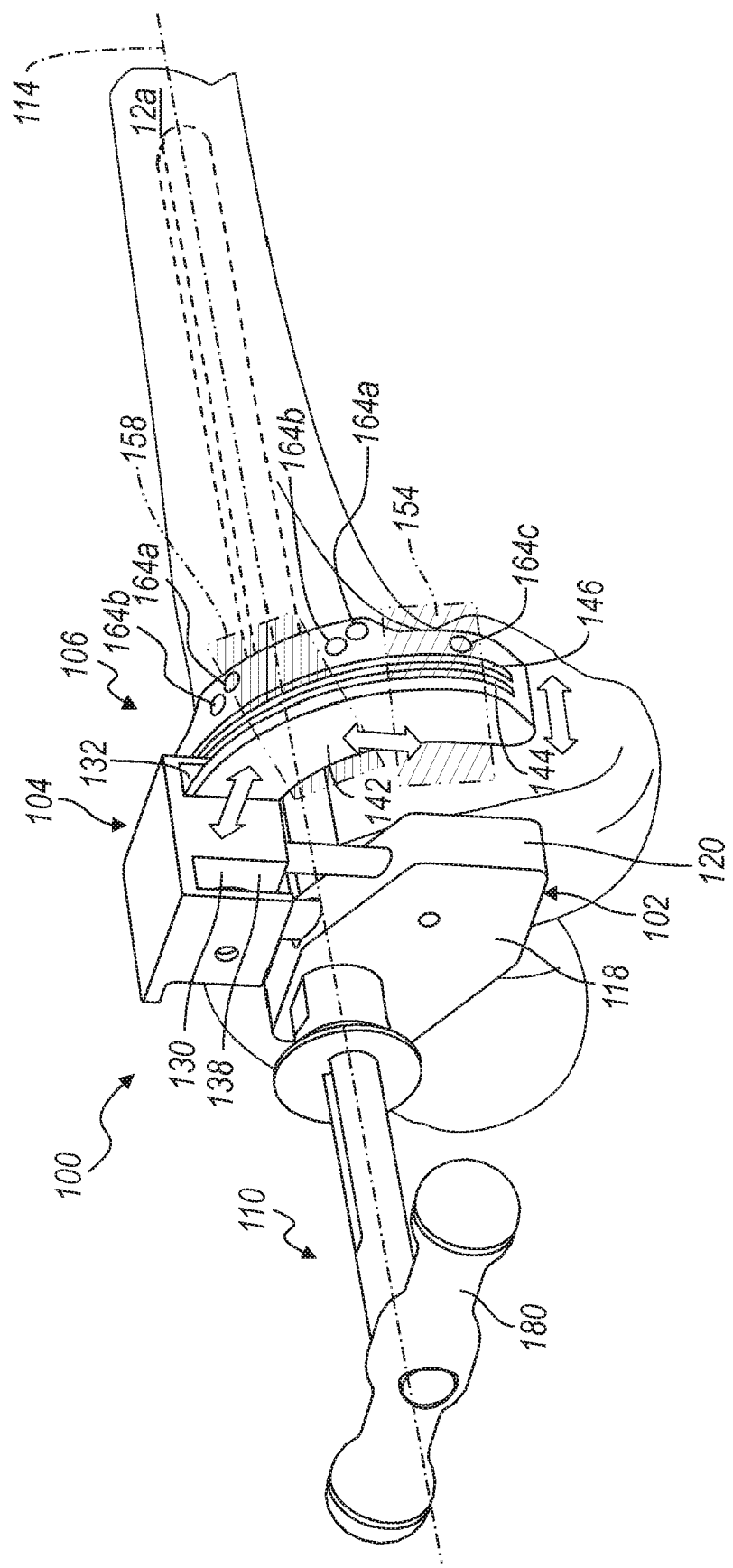
FIG. 6 is a perspective view of the distal femoral cutting guide assembly showing the distal femoral cutting guide assembly installed on a right femur in accordance with the present teachings.

In accordance with various aspects of the present teachings and with reference to FIG. 6, the cutting guide member 106 can be configured to be located over a medial anterior corner of the distal end of a right femur 12a. Moreover, the bridge member 104 can be configured to hold the cutting guide member 106 over the medial anterior portion of the distal end 20 of the femur 12. While holding the cutting guide member 106, the bridge member 104 can be configured to provide a sliding resistance between the cutting guide member 106 and the bridge member 104 in various aspects of the present teachings. The sliding resistance can be overcome by the medical professional as he or she repositions the cutting guide member 106 relative to the bridge member 104, which will be discussed in further detail herein.

Figure 7A:
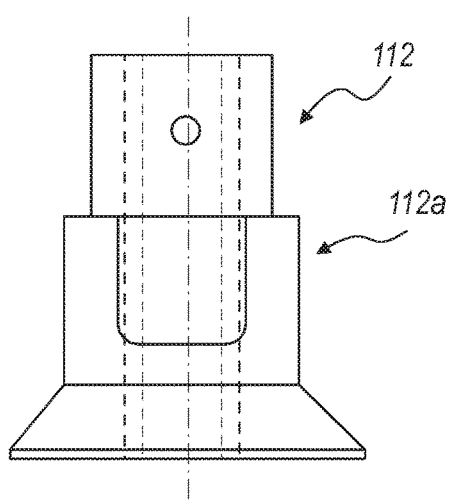
FIGS. 7A, 7B and 7C are each front views of different bushings showing the angle at which an intramedullary rod that can be received within the bushing would be disposed relative to the index member.
Figure 7B:
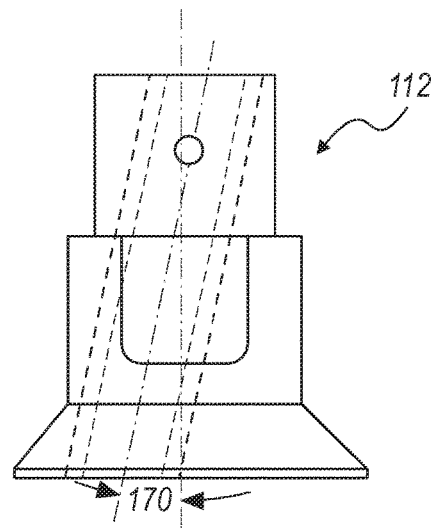
Figure 7C:
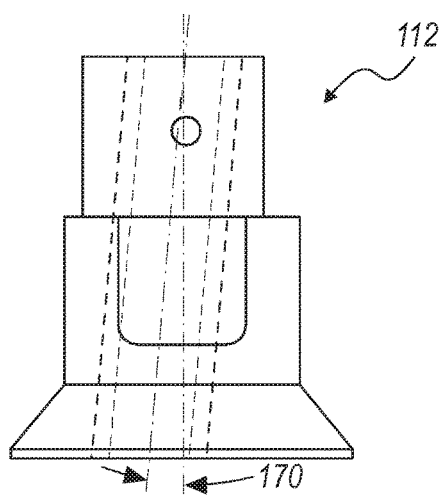

In accordance with one aspect of the present teachings and with reference to FIGS. 4 and 5A, the index member 102 can be coupled to an intramedullary rod 110 or other suitable mounting rod that can be inserted into the distal end 20 of the left femur 12b. A first bushing 112a can be selected from a plurality of bushings 112, examples of which are shown in FIGS. 7A, 7B and 7C. Each of the bushings 112 can couple to the index member 102 and can receive the intramedullary rod 110. Each of the bushings 112 can be configured to hold the index member 102 at a predetermined angle relative to a longitudinal axis 114 of the intramedullary rod 110, as discussed in greater detail.

Figure 3:
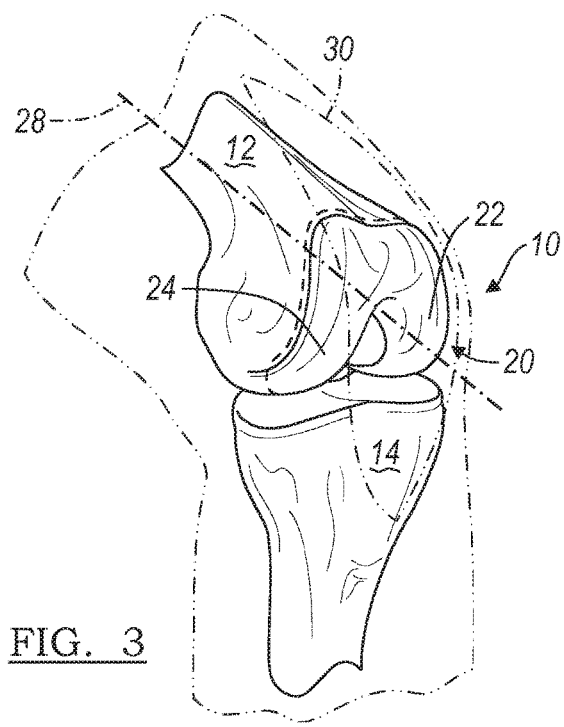
FIG. 3 is a perspective view of the knee joint, absent the muscle and the connective tissue, showing a lateral condyle, a medial condyle and an exemplary plane of resection of a distal end of the femur in accordance with the present teachings.

With reference to FIGS. 7A, 7B and 7C, the plurality of bushings 112 can, therefore, have varying configurations that provide for holding the index member 102 at a range of angles relative to the longitudinal axis 114 of the intramedullary rod 110 and, thus, the longitudinal axis 28 of the femur 12 (FIG. 3). The range of angles provided, for example, can include about four degrees to about seven degrees with about one degree angle increments between four and seven degrees. It will be appreciated that other configurations that provide more or less angle increments and/or the size of the increment can be implemented as applicable.

Returning to FIG. 4, the index member 102 can have a first surface portion 116 that can abut the distal end 20 of the femur 12 that can include one or more portions of the medial condyle 24 and the lateral condyle 22. A second surface portion 118 (FIG. 6) can be opposite the first surface portion 116 and one or more wall portions 120 can bound the first surface portion 116 and the second surface portion 118. The wall portions 120 can be configured in a shape that can be similar to a parallelogram, i.e., a quadrilateral with opposite sides parallel or something similar thereto. Notwithstanding, it will be appreciated in light of the disclosure that the index member 102 can be configured with various suitable polygonal shapes. Moreover, the wall portions 120 can further include connection to and/or be integrally formed with additional surfaces, facets, rounded portions, other suitable configurations and combinations thereof, that can be used to facilitate manipulation and insertion of the index member 102 through the incision 30 and/or a cannula.

The index member 102 can define a bushing receiving aperture 122. The bushing receiving aperture 122 can include wall portions 124 that can be configured to abut one of the bushings 112. Each of the bushings 112 can releasably couple to the index member 102 and/or can lock with the various suitable locking mechanisms thereto. One or more of the suitable locking mechanisms can securely hold one of the bushings 112 to the index member 102 but then can be uncoupled as needed.

The index member 102 can define one or more holes 126 that can receive one or more complementary posts 128 that can extend from the bridge member 104. The one or more of the holes 126 can be defined in the one or more wall portions 120 of the index member 102 and can be sized with different diameters or widths, as applicable, to receive the one or more complementary posts 128 on the bridge member 104. For example, a first post 128a can be received by a first hole 126a and, similarly, a second post 128b can be received by a second hole 126b. The first hole 126a and the first post 128a can have larger but complimentary diameters or width than the second post 128b and the second hole 126b that can have smaller but complementary diameters or widths, as applicable.

The combination of the holes 126 and the complementary posts 128 can be configured such that only a single orientation can exist in which the bridge member 104 can couple to the index member 102. In one example, as shown in FIG. 5B, the index member 102 can be oriented in a first position that can abut the distal end of the left femur 12b. With reference to FIG. 6, the index member 102 can be re-oriented so that the index member 102 is oriented in a second position and can abut the distal end of the right femur 12a. The bridge member 104 can also have a first orientation (FIG. 5B) and a second orientation (FIG. 6). With reference to FIG. 5B, the index member 102 that can abut the left femur 12b can be configured to only accept the bridge member 104 in the first orientation. With reference to FIG. 6, the index member 102 that can abut the right femur 12a can be configured to only accept the bridge member 104 in the second orientation.

Returning to FIG. 4, the bridge member 104 can define a first guide assembly 130 and a second guide assembly 132. The first guide assembly 130 can include a channel 134 that can be operable to receive and/or releasably couple a portion of the cutting guide member 106. One or more mounting mechanisms 136 can be mounted on one or more wall portions 138 within the channel 134 and can releasably couple the cutting guide member 106 to the first guide assembly 130. The one or more mounting mechanisms 136 can define one or more magnets, hook and loop fasteners, suitable adhesives and/or one or more suitable combinations thereof. It will be appreciated that one or more other mechanisms can be used to releasably couple the cutting guide member 106 to the one or more wall portions 138 of the first guide assembly 130. The one or more mounting mechanisms 136 and/or other suitable mechanisms can be made of, wholly or partially, one or more suitable biocompatible materials that can be sterilized.

The second guide assembly 132 can be similar to the first guide assembly 130 but can be positioned on an opposite side of the bridge member 104. The second guide assembly 132 can similarly include one or more mounting mechanisms 140 that can releasably couple the cutting guide member 106 to the bridge member 104. The one or more mounting mechanisms 140 and/or one or more other suitable fastening mechanisms can be mounted on one or more wall portions 142 in the second guide assembly 132 but at a location in the second guide assembly that can be opposite of a location of the one or more mounting mechanisms 136 in the first guide assembly 130.

Figure 5C:
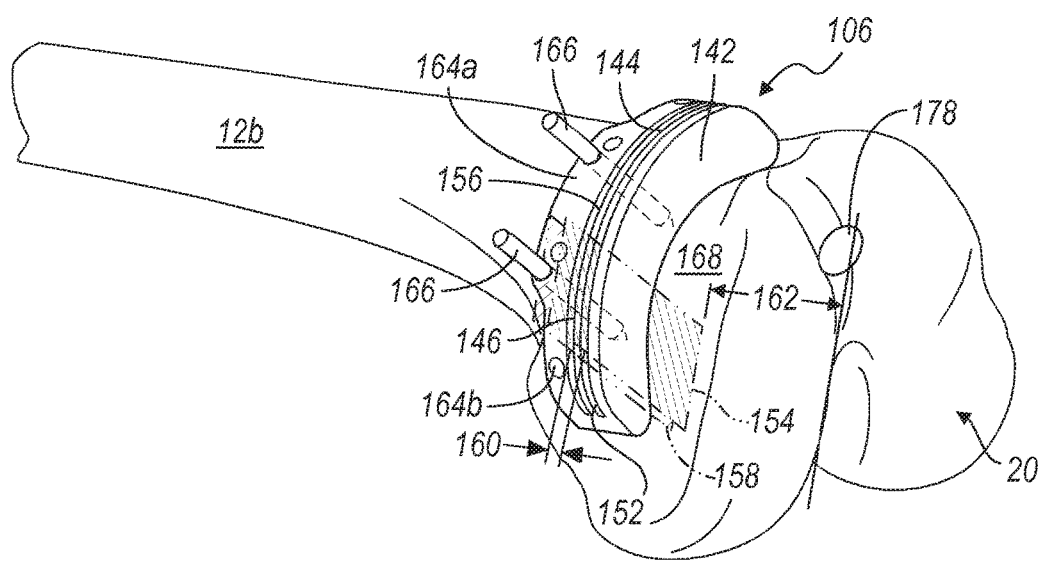
FIG. 5C is similar to FIG. 5A and shows the cutting guide member secured to the femur with two fixation pins in the first set of apertures.
Figure 5D:
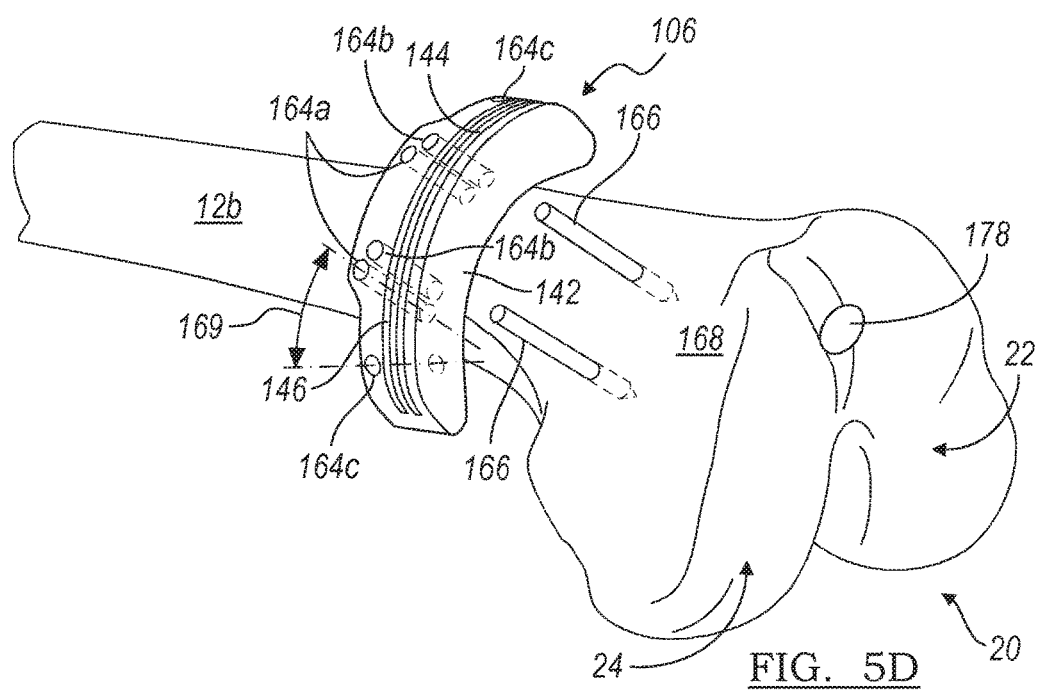
FIG. 5D is similar to FIG. 5C and shows the cutting guide member pulled off the fixation pins and the femur without the need to remove the fixation pins from the left femur.
Figure 5E:
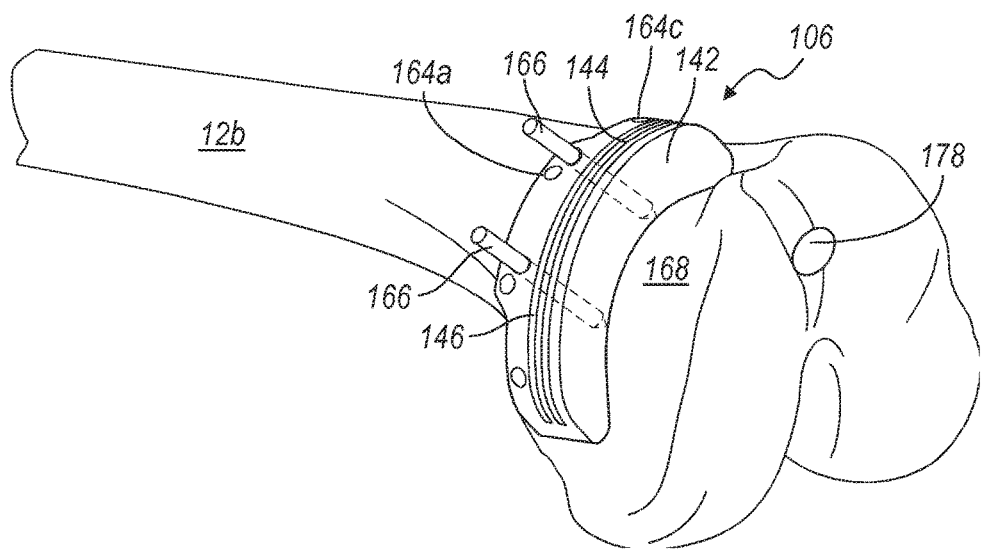
FIG. 5E is similar to FIG. 5C and shows the cutting guide member placed on the fixation pins that are received by additional apertures in the second set of apertures that position the cutting guide member in a superior direction, i.e., up the left femur.
Figure 5F:
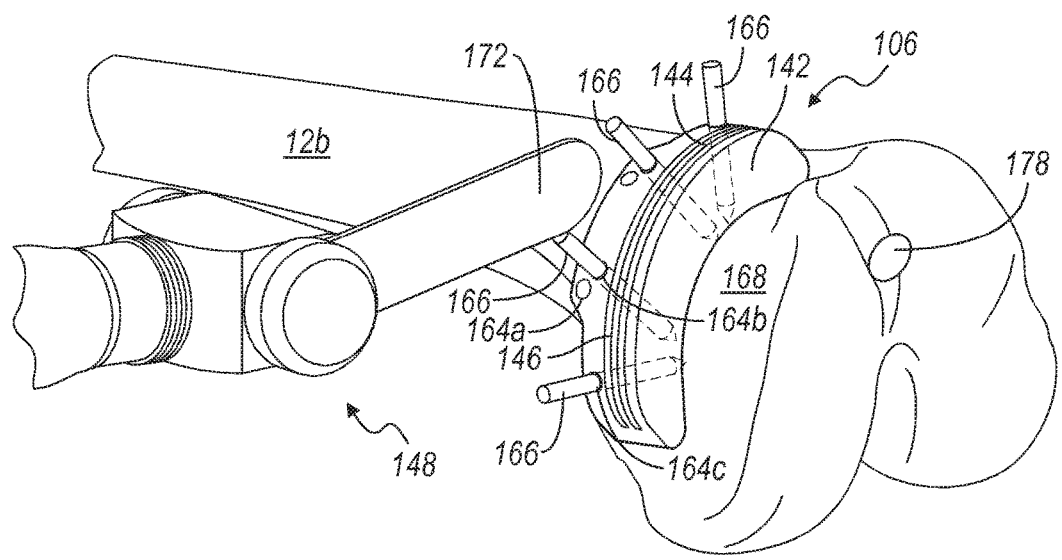
FIG. 5F is similar to FIG. 5E and shows the cutting guide member secured to the femur with the fixation pins through a second set and a third set of fixation apertures that can hold the cutting guide member to the femur, while an exemplary resecting tool can make a cut using the guide channels that establish a reference plane on which the resection can be based.

With reference to FIG. 6, the one or more mounting mechanisms 136, 140 in the first and the second guide assemblies 130, 132 can hold the cutting guide member 106, while the cutting guide member 106 can be adjusted relative to the distal end 20 of the femur 12a, 12b. After final adjustment, the cutting guide member 106 can be held by the bridge member 104 until a relatively more secure fastener can couple to the cutting guide member 106 to the femur 12a, 12b, an example of which is shown in FIG. 5F. During one or more adjustments, the mounting mechanisms 136, 140 can provide for a sliding resistance that can be overcome by a medical professional (not shown) when he or she repositions (i.e., the one or more adjustments) the cutting guide member 106 relative to the bridge member 104 and/or relative to the distal end 20 of the femur 12a, 12b.

Returning to FIG. 4, the cutting guide member 106 can generally define a body portion 142 having a first guide channel portion 144 and a second guide channel portion 146 that can be formed through the body portion 142 and can be spaced from one another. The first and the second channel portions 144, 146 can each define a generally elongated rectangular aperture through which a suitable tool 148 (FIG. 5F), such as a manual or a powered resecting tool, can be placed for cutting a portion of the distal end 20 of the femur 12, as shown in FIG. 5C. One or more wall portions 152 of the first guide channel portions 144 can establish the first reference plane 154 on which a resection of the medial anterior portion 150 of the femur 12 can be performed. In addition, the one or more wall portions 156 of the second guide channel 146 can establish a second reference plane 158.

The body portion 142 of the cutting guide member 106 can define a generally arcuate shape. The generally arcuate shape can be configured to fit over a medial anterior portion 150 of the femur 12a, 12b. It will be appreciated in light of the disclosure the arcuate shape can be configured to be disposed over a medial surface and an anterior surface of the distal end 20 of the femur 12. In this position, the arcuate shape of the cutting guide member 106 can be disposed over a portion of the medial anterior corner of the femur 12.

The first cutting channel 144 and the second cutting channel 146 can be configured with a similar size and/or shape but can be spaced from one another a predetermined distance 160. In one example, the predetermined distance 160 can be sufficient enough to provide about a three millimeter difference in a distal cutting depth 162 (FIG. 5C) between a resection based on the first reference plane 154 and a resection based on the second reference plane 158. By way of the above example, the medical professional can resect a portion of the femur 12 by placing the suitable resecting tool 148 through the first guide channel 144. The resecting tool 148 (FIG. 5F) can also cut an additional three millimeters from the femur 12a, 12b by placing the resecting tool 148 through the second guide channel 146 and cutting the distal end 20 of the femur 12a, 12b based on the second reference plane 158 established by the second guide channel 146.

The body portion 142 of the cutting guide member 106 can include a plurality of apertures 164. Each of the apertures 164 can receive one or more fixation pins 166. The plurality of apertures 164 can include at least a first set of apertures 164a, a second set of apertures 164b and a third set of apertures 164c. With the cutting guide member 106 secured to the femur 12a, 12b with the fixation pins 166 either in the first set of apertures 164a or in the second set of apertures 164b, the cutting guide member 106 can still be removed from the femur 12 without the need to remove the fixation pins 166. In this regard, the first set of apertures 164a and the second set of apertures 164b are configured so as to permit the cutting guide member 106 to be lifted off the femur 12a, 12b with the fixation pins 166 remaining, as shown, for example, in FIG. 5D.

In contrast, the third set of apertures 164c are configured such that when the cutting guide member 106 is fixed to the femur 12 using the third set of apertures 164c, the cutting guide member 106 can only be removed from the femur 12a, 12b by removing the fixation pins 166 from the third set of apertures 164c. As such, securing the cutting guide member 106 to the femur 12a, 12b with the third set of apertures 164c (FIG. 5F) relative to the first set of apertures 164a (FIG. 5C) can be shown to provide a relatively more robust securement during a resection procedure. The fixation pins 166, however, need to be removed from the third set of apertures 164c before the cutting guide member 106 can be removed from the femur 12.

In one example, when one or more of the fixation pins 166 are in the first set of apertures 164a, the fixation pins 166 are disposed generally normal to an exterior surface 168 of the femur 12a, 12b. Because the fixation pins 166 are generally normal to the exterior surface 168, the cutting guide member 106 can be secured from rotation and/or displacement in directions that are generally parallel to the longitudinal axis 114 (FIG. 6) of the femur 12a, 12b.

The cutting guide member 106, however, can be pulled away from the exterior surface 168 of the femur 12a, 12b so that the cutting guide member 106 can be, for example, repositioned. In this regard, the cutting guide member 106 can be advanced up (i.e., in a superior direction) or down (i.e., in an inferior direction) relative to the longitudinal axis 114 of the femur 12 to adjust the reference planes 154, 158 for a more deep or a more shallow resection of the distal end 20 of the femur 12 (see, e.g., FIGS. 5C, 50, 5E and 5F). In doing so, the first set of apertures 164a can release the fixation pins 166 and the second set of apertures 164b can receive the fixation pins 166 so that the cutting guide member 106 can be located in a more superior position. In contrast, the third set of apertures 164c in the cutting guide member 106 can be at an angle 169 (FIG. 5D) that, in certain aspects, is not parallel to the first and second set of apertures 164a, 164b. The configuration of the angle 169 allows the cutting guide member 106 to be relatively more securely fastened to the femur 12a, 12b in that the cutting guide member 106 may not lift off the femur 12a, 12b while the fixation pins 166 are received by the third set of apertures 164c.

With reference to FIG. 5F, the suitable resecting tool 148 can be manual or powered. A powered implementation of the resecting tool 148 can be electrical and/or pneumatic. A portion of the resecting tool 148, for example, a blade 172 can index off (e.g., abut while reciprocating) one of the first cutting channel 144 or the second cutting channel 146 formed in the cutting guide member 106. In this regard, the resecting tool 148 can cut along (or cut generally parallel to) the reference plane 154 established by the first cutting channel 144 or the second reference plane 158 established by the second cutting channel 146.

With reference to FIG. 5A, the intramedullary rod 110 can be configured to fit into an intramedullary canal 176. In one example, the intramedullary rod 110 can be inserted in a hole 178 formed between the condyles 22, 24 of the distal end 20 of the femur 12. It will be appreciated in light of the disclosure that the intramedullary rod 110 can be inserted in the hole 178, a sufficient distance so that various components can be installed on an end of the intramedullary rod 110 that is not disposed in the intramedullary canal 176. A portion of the intramedullary rod 110 can be configured to accept a removable handle 180 that can be used to facilitate installation and/or removal of the intramedullary rod 110 in and from the intramedullary canal 176 and/or to facilitate installation or removal of various components on and from the intramedullary rod 110.

With reference to FIG. 4A, a cross-section 182 of the intramedullary rod 110 can be generally oval but can include one or more portions that can be removed from an otherwise whole oval-shape. In one example, two v-shaped grooves 184 can be formed at generally opposite sides of the intramedullary rod 110. The v-shaped grooves 184 or other suitable portions removed from the intramedullary rod 110 can provide for an anti-rotation functionality. In this regard, one or more components that can be inserted on the intramedullary rod 110 can be keyed (i.e., include key to interconnect with one of the grooves 184) to provide an anti-rotation functionality.

The various components of the cutting guide assembly 100 can be made of one or more suitable bio-compatible materials. One example of a bio-compatible material is a cobalt chrome alloy. Other examples can include titanium and suitable polymers such as an ultra high molecular weight polyethylene.

With reference to FIGS. 4, 7A, 7B, 7C, the bushing 112 can couple the intramedullary rod 110 to the index member 102. The bushing 112 can be configured such that the intramedullary rod 110 can be held at the angle 170 relative to the index member 102. In this regard, the angle 170 can range from negative four to positive four degrees. As explained above, one bushing 112a can be selected from the plurality of bushings 112 to select a predetermined angle between the intramedullary rod 110 and the index member 102. As such, each bushing 112 of the plurality of bushings 112 can be configured to provide a different angle between the longitudinal axis 114 of the intramedullary rod 110 and the index member 102.

In operation, one or more incisions 30 can be made near the knee joint 10 to provide access to a portion of the distal end 20 of the femur 12, as shown in FIG. 3. With reference to FIGS. 4-5F, the intramedullary rod 110 can be mounted into the hole 178 (FIG. 5C) formed in the distal end 20 of the femur 12. The handle 180 can be removed from the intramedullary rod 110 to provide access and to allow for components to be inserted over the intramedullary rod 110. One of the bushings 112 can be selected from the plurality of bushings 112 (FIGS. 7A-7C) to establish, for example, the reference plane 108, 154, 158 that is disposed at the angle 170 (FIGS. 7A-7C) relative to the longitudinal axis 114 of the intramedullary rod 110. The angle 170 can be a suitable valgus angle as determined by the medical practitioner.

When one of the proper bushings 112 is selected, the bushing 112 can be coupled to the index member 102. The bridge member 104 can be coupled to the index member 102. The cutting guide member 106 can then be coupled to the index member 102 and held in place in the first guide assembly 130 by the one or more mounting mechanisms 140 or other suitable fasteners. The index member 102, the bridge member 104 and the cutting guide member 106 can be inserted over the intramedullary rod 110 via the bushing 112 and slid down the intramedullary rod 110 to abut the distal end 20 of the femur 12.

When the index member 102 abuts the distal end 20 of the femur 12, the cutting guide member 106 can be manipulated so as to be positioned around the medial anterior portion 150 of the distal end 20 of the femur 12. In this regard, the arcuate shape of the cutting guide member 106 can be disposed around the medial anterior portion 150 of the femur 12a, 12b to provide the access to that portion of the femur 12a, 12b.

The cutting guide member 106 can be releasably coupled to the bridge member 104 so as to provide a sliding resistance between the cutting guide member 106 and the bridge member 104. It will be appreciated in light of this disclosure that the medical professional can overcome the sliding resistance as he or she manipulates the cutting guide member 106 relative to the femur 12 as he or she positions the cutting guide member 106 about the medial anterior portion of the distal end 20 of the femur 12.

With reference to FIG. 5F, when the cutting guide member 106 is positioned as described above, one or more of the fixation pins 166 can be driven into the first set of apertures 164a formed on the body portion 142 of the cutting guide member 106. One or more additional fixation pins 166 can be inserted through the third set of apertures 164c formed in the body portion 142 of the cutting guide member 106. Resection of the distal end 20 of the femur 12a, 12b along the first reference plane 154 established by the first channel portion 144 can occur with the cutting guide member 106 secured to the femur 12 with the fixation pins 166 in one of the first set of apertures 164a, the second set of apertures 164b, the third set of apertures 164c and one or more combinations thereof. When the fixation pins 166 are received in the third set of apertures 164c, the fixation pins 166 can be removed so as to allow the cutting guide member 106 to be lifted off the fixation pins 166 received in the first set of apertures 164a and, for example, advanced up in a direction superior to the distal end 20 of the femur 12 and then re-secured by allowing the second set of apertures 164b to receive the same fixation pins 166. In this regard, the cutting guide member 106 is advanced up the femur 12a, 12b a predetermined distance.

Prior to or after the advancement of the cutting guide member 106 of the femur 12a, 12b, the medical practitioner can continue to resect the distal end 20 of the femur 12a, 12b using the first cutting channel 144 or the second cutting channel 146, which can be at a predetermined distance from the first cutting channel 144.

While specific aspects have been described in this specification and illustrated in the drawings, it will be understood by those skilled in the art in light of the disclosure that various changes can be made and equivalents can be substituted for elements thereof without departing from the scope of the present teachings, as defined in the claims. Furthermore, the mixing and matching of features, elements and/or functions between various aspects of the present teachings are expressly contemplated herein so that one skilled in the art will appreciate from the present teachings that features, elements and/or functions of one aspect of the present teachings may be incorporated into another aspect, as appropriate, unless described otherwise above. Moreover, many modifications may be made to adapt a particular situation, configuration and/or material to the present teachings without departing from the essential scope thereof. Therefore, it is intended that the present teachings not be limited to the particular aspects illustrated by the drawings and described in the specification as the best mode presently contemplated for carrying out the present teachings but that the scope of the present teachings will include many aspects and examples following within the foregoing description and the appended claims.

What is claimed is:

1. A system for locating a femoral cutting guide on a distal end of a femur that establishes at least a first reference plane to perform a distal femoral planar cut, the system comprising:
    a cutting guide member configured to fit against the femur, wherein the cutting guide member has a first cutting channel defining the first reference plane;
    a bridge member configured to orient the cutting guide member relative to the distal end of the femur and having a first portion insertable in the first cutting channel, wherein the bridge member and first cutting channel are configured to allow movement of the cutting guide member relative to the bridge member along a first direction; and
    a mounting mechanism configured to releasably couple the bridge member to the cutting guide member.

2. The system of claim 1, further comprising:
    an index member mountable on an intramedullary rod and configured to abut the distal end of the femur, wherein the index member has a first aperture, and wherein the bridge member has a first elongated post removably receivable in the first aperture.

3. The system of claim 2, further comprising a bushing selectable from a plurality of bushings for removably coupling the index member to the intramedullary rod with the bushing creating a desired an between index member and the intramedullary rod.

4. The system of claim 1, wherein the bridge member has a first channel configured to receive a distal portion of the cutting guide member therein, and wherein the first portion includes a projection that forms a wall of the first channel and the projection is insertable in the first cutting channel.

5. The system of claim 4, wherein the projection is configured to inhibit movement of the cutting guide member in a superior-distal direction relative to the femur but is configured allow movement of the cutting guide member along the first direction.

6. The system of claim 4, wherein the mounting mechanism is carried by the bridge member and is positioned on the bridge member to interface the first channel so as to interface with the distal portion of the cutting guide member when the first portion of the bridge member is inserted in the first cutting channel.

7. The system of claim 1, wherein the bridge member is configured to inhibit movement of the cutting guide member in a superior-distal direction relative to the femur.

8. The system of claim 1, wherein the bridge member has a bisymmetrical shape so as to include second portion shaped as a mirror image of the first portion to allow the bridge member to be used on either a left femur or a right femur by reversing an orientation of the first portion and the second portion.

9. The system of claim 1, wherein the mounting mechanism comprises one or more of a magnet, hook and loop fastener, and an adhesive, and wherein the mounting mechanism is configured to generate a sliding resistance between the bridge member and the cutting guide member.

10. A system for locating a femoral cutting guide on a distal end of a femur that establishes at least a first reference plane to perform a distal femoral planar cut, the system comprising:
    an index member configured to abut the distal end of the femur;
    a cutting guide member configured to fit against the femur, wherein the cutting guide member has a first cutting channel defining the first reference plane; and a bridge member configured to orient the cutting guide member relative to the distal end of the femur and configured to couple with the index member, wherein the bridge member has a first portion insertable in the first cutting channel, and wherein the bridge member and first cutting channel configured to allow movement of the cutting guide member relative thereto along a first direction.

11. The system of claim 10, wherein the bridge member has a bisymmetrical shape so as to include second portion shaped as a mirror image of the first portion to allow the bridge member to be used on either a left femur or a right femur by reversing an orientation of the first portion and the second portion, and wherein the bridge member defines an orientation specific coupling such that the bridge member in the first orientation only couples to the index member in the first orientation.

12. The system of claim 10, further comprising:
an intramedullary rod configured to insert into the distal end of the femur; and
a bushing having an aperture corresponding to the shape of the cross-section of the intramedullary rod for receiving the intramedullary rod;
wherein the index member is configured to receive the bushing and has an angle relate e to the intramedullary rod defined by the bushing.

13. The system of claim 12, wherein the bushing is selectable from a plurality of bushings, each of the plurality of bushings configured to define a different angle between the index member and the intramedullary rod.

14. The system of claim 12, further comprising:
a mounting mechanism that is configured to releasably couple the bridge member to the cutting guide member, wherein the mounting mechanism is configured to generate a sliding resistance between the bridge member and the cutting guide member.

15. The system of claim 12, wherein the intramedullary rod has an oval cross-section with first and second opposing cut-out grooves configured to reduce a propensity of the intramedullary rod to rotate after insertion of the intramedullary rod into the distal femur.

16. The system of claim 10, wherein the bridge member has a first channel configured to receive a distal portion of the cutting guide member therein, and wherein the first portion includes a projection that forms a wall of the first channel and the projection is insertable in the first cutting channel.

17. The system of claim 16, wherein the projection is configured to inhibit movement of the cutting guide member in a superior-distal direction relative to the femur but is configured allow movement of the cutting guide member along the first direction.

18. A system for locating a femoral cutting guide on a distal end of a femur, the system comprising:
an index member configured to abut the distal end of the femur;
a bridge member configured to couple with the index member and configured to couple with and orient the femoral cutting guide relative to the distal end of the femur;
wherein the bridge member has a bisymmetrical shape so as to include a second portion shaped as a minor image of a first portion to allow the bridge member to be used on either a left femur or a right femur by reversing an orientation of the first portion and the second portion, and wherein the bridge member defines an orientation specific coupling such that the bridge member in a first orientation only couples to the index member in the first orientation; and
a cutting guide member configured to fit against a distal portion of the femur, wherein the cutting guide member has a first cutting channel defining a first reference plane to perform a distal femoral planar cut;
wherein the bridge member has a first portion insertable in the first cutting channel, the bridge member and first cutting channel configured to allow movement of the cutting guide member relative thereto along a first direction.

19. The system of claim 18, further comprising:
a mounting mechanism that is configured to releasably couple the bridge member to the cutting guide member, wherein the mounting mechanism is configured to generate a sliding resistance between the bridge member and the cutting guide member.

20. The system of claim 18, further comprising:
an intramedullary rod configured to insert into the distal end of the femur; and
a bushing having an aperture corresponding to the shape of the cross-section of the intramedullary rod for receiving the intramedullary rod;
wherein the index member is configured to receive the intramedullary rod and has an angle relative thereto defined by the bushing.

* * * * *

UNITED STATES PATENT AND TRADEMARK OFFICE
CERTIFICATE OF CORRECTION

PATENT NO. : 10,238,399 B2
APPLICATION NO. : 15/787159
DATED : March 26, 2019
INVENTOR(S) : Fox et al.

It is certified that error appears in the above-identified patent and that said Letters Patent is hereby corrected as shown below:

On the Title Page

Item (57), in "Abstract", in Column 2, Line 7, delete "medal" and insert --madial-- therefor In the Claims In Column 10, Line 27, in Claim 3, delete "an" and insert --angle-- therefor In Column 11, Line 25, in Claim 12, delete "relate e" and insert --relative-- therefor In Column 12, Line 15, in Claim 18, delete "minor" and insert --mirror-- therefor Signed and Sealed this
Fifth Day of May, 2020

Andrei Iancu
*Director of the United States Patent and Trademark Office*